(12) United States Patent
Kim et al.

(10) Patent No.: US 10,149,708 B2
(45) Date of Patent: Dec. 11, 2018

(54) BONE PLATE SYSTEM

(71) Applicant: JEIL MEDICAL COPORATION, Seoul (KR)

(72) Inventors: Chan Bong Kim, Seongnam-si (KR); Jang Hyeon Seo, Gimpo-si (KR); Sung Kyu Choi, Gwangmyeong-si (KR)

(73) Assignee: JEIL MEDICAL COPORATION, Seoul (KR)

( * ) Notice: Subject to any disclaimer, the term of this patent is extended or adjusted under 35 U.S.C. 154(b) by 259 days.

(21) Appl. No.: 15/052,479

(22) Filed: Feb. 24, 2016

(65) Prior Publication Data
US 2016/0242829 A1  Aug. 25, 2016

(51) Int. Cl.
*A61B 17/80* (2006.01)

(52) U.S. Cl.
CPC ...... *A61B 17/8057* (2013.01); *A61B 17/8052* (2013.01)

(58) Field of Classification Search
CPC .......... A61B 17/8052; A61B 17/8057
See application file for complete search history.

(56) References Cited

U.S. PATENT DOCUMENTS

| 9,877,754 | B2 * | 1/2018 | Patel | A61B 17/8014 |
| 2004/0073218 | A1 * | 4/2004 | Dahners | A61B 17/8057 606/287 |
| 2007/0093836 | A1 * | 4/2007 | Derouet | A61B 17/8052 606/86 A |
| 2008/0208259 | A1 * | 8/2008 | Gilbert | A61B 17/8057 606/280 |
| 2008/0300637 | A1 * | 12/2008 | Austin | A61B 17/74 606/290 |
| 2010/0160973 | A1 * | 6/2010 | Leung | A61B 17/8014 606/289 |
| 2010/0312286 | A1 * | 12/2010 | Dell'Oca | A61B 17/8057 606/291 |
| 2011/0015681 | A1 * | 1/2011 | Elsbury | A61B 17/7059 606/286 |
| 2011/0301608 | A1 * | 12/2011 | Roth | A61B 17/8052 606/70 |
| 2014/0018862 | A1 * | 1/2014 | Koay | A61B 17/8057 606/281 |

(Continued)

FOREIGN PATENT DOCUMENTS

| JP | 2013-529484 A | 7/2013 |
| JP | 2015-027474 A | 2/2015 |

(Continued)

*Primary Examiner* — David Bates
(74) *Attorney, Agent, or Firm* — Novick, Kim & Lee, PLLC; Jae Youn Kim (57) ABSTRACT

A bone plate system for fracture surgery is provided. The bone plate system includes a bone plate and a locking screw. The bone plate includes an upper surface, a lower surface facing a bone, and a locking hole in which an even-number-ridge internal thread is formed. The locking screw is coupled to the locking hole. The locking screw includes a head tapered so that a diameter thereof decreases along a center axis, a shank extending from the head, a double-ridge external thread formed on the head and configured to be tightened to the even-number-ridge internal thread, and an external thread formed on the shank and configured to be fastened to the bone.

6 Claims, 11 Drawing Sheets

(56) References Cited

U.S. PATENT DOCUMENTS

| | | | | |
|---|---|---|---|---|
| 2014/0271028 A1* | 9/2014 | Arnett | ............... | F16B 39/28 |
| | | | | 411/259 |
| 2018/0021071 A1* | 1/2018 | Thiel | ............ | A61B 17/8009 |
| | | | | 606/281 |
| 2018/0064477 A1* | 3/2018 | Lopez | ............ | A61B 17/8033 |

FOREIGN PATENT DOCUMENTS

| | | | |
|---|---|---|---|
| KR | 10-2014-0144564 A | 12/2014 | |
| KR | 10-1471627 B1 | 12/2014 | |

\* cited by examiner

BONE PLATE SYSTEM

TECHNICAL FIELD

The present invention relates to a bone plate system and, more particularly, to a bone plate system for fracture surgery.

BACKGROUND ART

For the purpose of fracture surgery, a bone plate system is configured to press fractured bone fragments against each other and to pull bone fragments into contact with each other, thereby promoting treatment thereof. The bone plate system includes a bone plate and bone screws. The bone plate may have a hole in which an internal thread is formed and a hole in which an internal thread is not formed. The bone screws include a locking screw having a head on which an external thread is formed and a non-locking screw having a head on which an external thread is not formed. Each of the locking screw and the non-locking screw is provided with a shank on which an external thread to be coupled to a bone is formed.

The external thread formed on the head of the locking screw is coupled to the internal thread of the bone plate, thereby fixing an angle at which the shank is coupled to a bone. The locking screw is coupled so that the center axis thereof is coaxial with the center axis of the internal thread. Furthermore, the locking screw can prevent itself from being untightened or loosened by a dynamic load acting on the bone fragments and the bone plate after a surgical operation. However, the locking screw has a limited bone fragment pressing ability which affects a fracture treatment.

The external thread of the non-locking screw may be coupled to a bone at different angles. However, the non-locking screw is not fixed to the bone plate because an external thread is not formed in the head thereof. Thus, during or after a surgical operation, the angle between the bone plate and the non-locking screw may be changed. Furthermore, the non-locking screw may be untightened or loosened by a dynamic load acting on the bone fragments and the bone plate after a surgical operation. Thus may lead to an insufficient treatment. That is to say, the locking screw is capable of fixing a bonding angle of bone fragments but is limited in its insertion angle and its pressing ability. The non-locking screw is capable of being inserted into a bone at different desired angles to press bone fragments but has a drawback in that the non-locking screw may be loosened.

Korean Patent No. 10-1471627 entitled "bone plate system" and Korean Patent Application Publication No. 10-2014-0144564 entitled "bone plate system", both of which are filed by the assignee of the subject application, disclose a bone plate and a locking screw. The bone plate has a lower surface facing a bone, an upper surface, and an internal thread formed in a hole extending from the upper surface to the lower surface. The locking screw includes a head and a shank extending from the head in an axial direction and having an external thread to be coupled to a bone. The head has an external thread formed in a tapered portion whose diameter decreases along an axial direction. The external thread of the head is tightened to the internal thread of the bone plate so that the angle of the locking screw can be adjusted. The disclosures of the patent documents cited above are incorporated herein by reference.

In the bone plate systems mentioned above, a strong fixing force is required in order to stably fix a bone. Moreover, it is required that the fixing force generated by tightening a screw can be transmitted to a bone via the bone plate. Accordingly, a demand has existed for a bone plate system which can generate a strong fixing force during fracture surgery and which can be easily used by a surgeon.

SUMMARY OF THE INVENTION

The present invention seeks for solution to overcome the aforementioned problems inherent in the bone plate systems of related art.

It is an object of the present invention to provide a novel bone plate system capable of increasing a fixing force.

Another object of the present invention is to provide a bone plate system capable of making it easy to tighten a locking screw and capable of enhancing the ease of fracture surgery.

A further object of the present invention is to provide a bone plate system capable of increasing a tightening angle of a locking screw.

According to one aspect of the present invention, there is provided a bone plate system, including:

a bone plate including an upper surface, a lower surface facing a bone, and a locking hole in which an even-number-ridge internal thread is formed; and a locking screw coupled to the locking hole, the locking screw including a head tapered so that a diameter thereof decreases along a center axis, a shank extending from the head, a double-ridge external thread formed on the head and configured to be tightened to the even-number-ridge internal thread, and an external thread formed on the shank and configured to be fastened to the bone, wherein the even-number-ridge internal thread and the double-ridge external thread are equal in lead to each other, a depth of a valley having a maximum major diameter among valleys of the double-ridge external thread is set larger than a height of ridges of the even-number-ridge internal thread so that when the double-ridge external thread is tightened to the even-number-ridge internal thread, the locking screw is obliquely tightened with respect to a center axis of the locking hole, and a plurality of screw entry guide grooves is formed at ridge start points of the even-number-ridge internal thread so as to guide entry of the double-ridge external thread.

In the bone plate system, each of the screw entry guide grooves is formed to extend along a lead angle of the even-number-ridge internal thread, each of the screw entry guide grooves including a start end portion and a terminal end portion, the terminal end portion being larger in depth than the start end portion.

In the bone plate system according to the present invention, the fixing force of the bone plate and the locking screw can be increased by the coupling of the even-number-ridge internal thread and the double-ridge external thread. Furthermore, the screw entry guide grooves formed at the ridge start points of the even-number-ridge internal thread facilitate the tightening of the locking screw. This makes it possible to improve the ease of fracture surgery and to increase the tightening angle of the locking screw.

BRIEF DESCRIPTION OF THE DRAWINGS

The above and other objects and features of the present invention will become apparent from the following description of preferred embodiments, given in conjunction with the accompanying drawings.

DETAILED DESCRIPTION OF THE PREFERRED EMBODIMENTS

Preferred embodiments of a bone plate system according to the present invention will now be described in detail with reference to the accompanying drawings.

Figure 1:
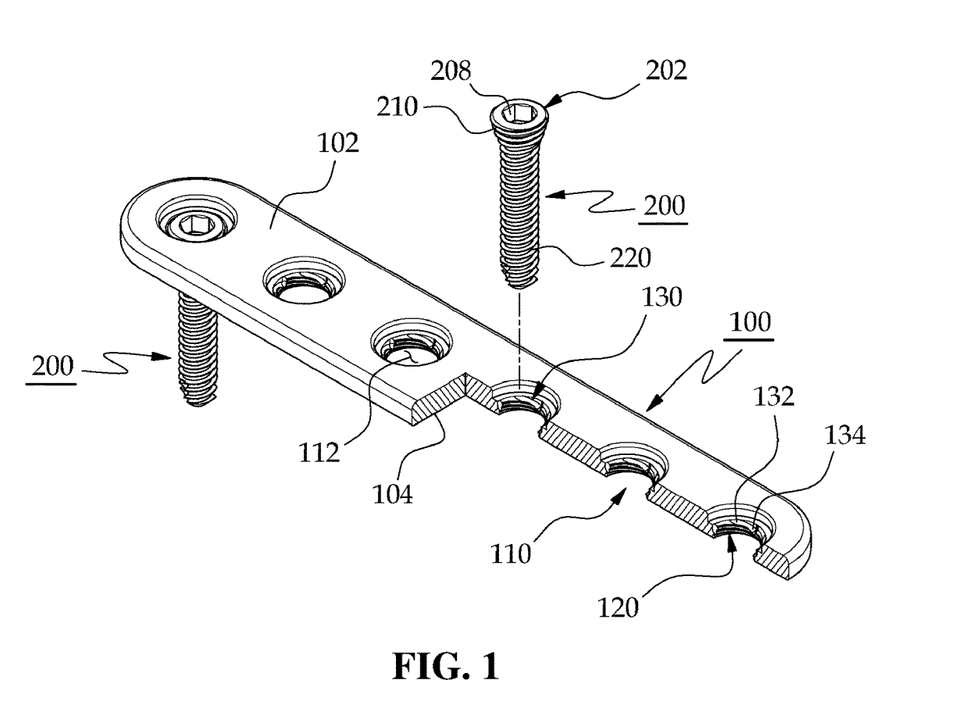
FIG. 1 is a perspective view illustrating a bone plate system according to the present invention.

Referring first to FIG. 1, the bone plate system according to the present invention includes a bone plate 100 and a locking screw 200. In order to maintain a stable function within a living body for fracture surgery, the bone plate 100 may preferably be made of a material, which is superior in mechanical characteristics and which has bio-compatibility and bio-functionability, for example, titanium. However, the material of the bone plate 100 is not limited thereto.

Figure 2A:
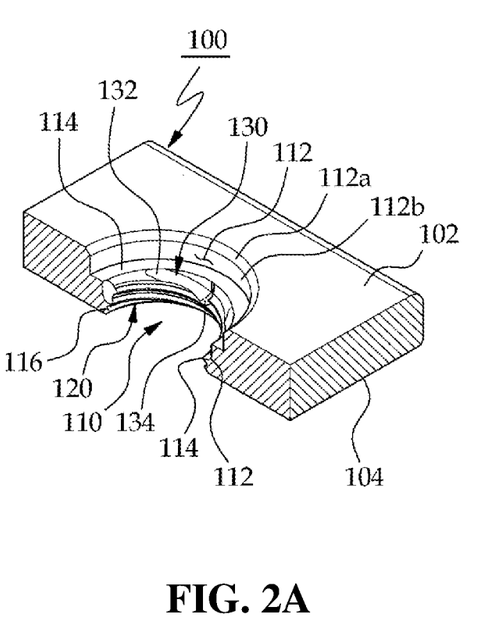
FIGS. 2A and 2B are perspective plan views illustrating a bone plate employed in the bone plate system according to the present invention.
Figure 2B:
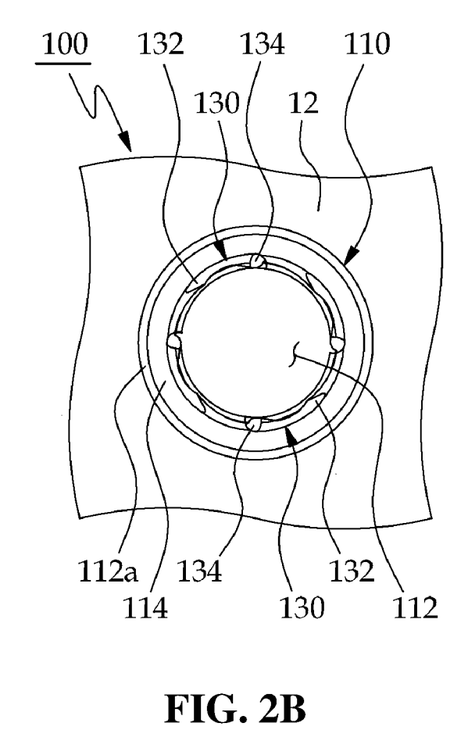

Referring to FIGS. 1 and 2, the bone plate 100 includes an upper surface 102, a lower surface 104 disposed so as to face a bone, and one or more locking holes 110 as screw holes which extend through the upper surface 102 and the lower surface 104. In some embodiments, the bone plate 100 may include a compression hole for the tightening of a non-locking screw, a small hole for the fixing of a K-wire, and a translation slot formed for position adjustment. The compression hole is a hole in which an internal thread is not formed. A non-locking screw is inserted into the compression hole and is fixed to a bone. The K-wire is a pin which is implanted to bone fragments to hold the bone fragments in place. Furthermore, the bone plate 100 may be bent so that the lower surface 104 makes close contact with a bone.

Each of the locking holes 110 includes a bore 112 and a four-ridge internal thread 120 as an even-number-ridge internal thread formed on an inner circumferential surface of the bore 112. The four-ridge internal thread 120 includes a plurality of valleys 122, a plurality of ridges 124, and a plurality of flanks 126 which interconnects the valleys 122 and the ridges 124 adjoining each other. The four-ridge internal thread 120 has four ridge start points corresponding to the respective ridges 124. The four ridge start points are disposed at an interval of 90 degrees. In some embodiments, the even-number-ridge internal thread may be configured by a double-ridge internal thread or a six-ridge internal thread, although the four-ridge internal thread 120 is illustrated herein.

A plurality of screw entry guide grooves 130 is formed at the ridge start points of the four-ridge internal thread 120 so that the screw entry guide grooves 130 are connected to the four-ridge internal thread 120. Each of the screw entry guide grooves 130 is formed to extend along a lead angle of the four-ridge internal thread 120. Each of the screw entry guide grooves 130 is formed such that the depth of a start end portion 132 thereof becomes larger than the depth of a terminal end portion 134 thereof. Furthermore, each of the screw entry guide grooves 130 is formed to have a width gradually increasing from the start end portion 132 toward the terminal end portion 134. In some embodiments, each of the screw entry guide grooves 130 may be formed to have a width kept constant from the start end portion 132 to the terminal end portion 134. The screw entry guide grooves 130 may be formed by milling which uses an end mill.

Figure 3A:
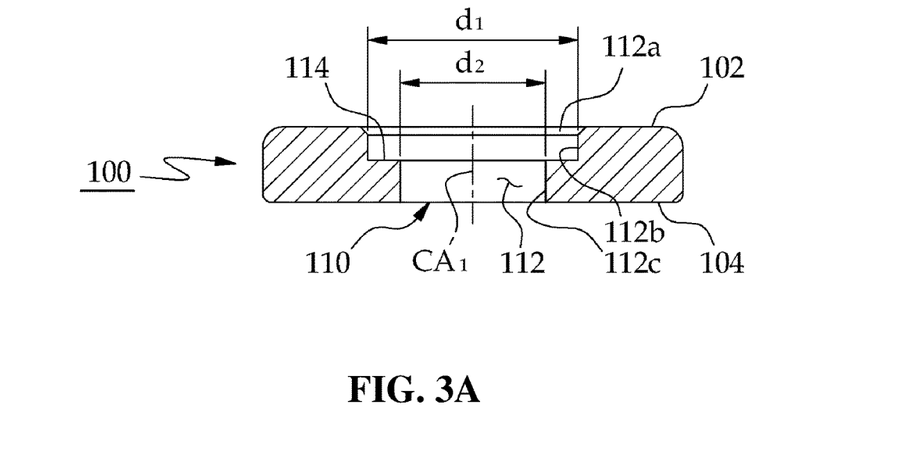
FIGS. 3A and 3B are sectional views for explaining a process of forming the locking hole shown in FIG. 2.

The bore and the four-ridge internal thread of each of the locking holes of the bone plate will be described with reference to FIGS. 3A and 3B. As illustrated in FIG. 3A, the bore 112, in which the four-ridge internal thread 120 is not formed as yet, includes an upper portion 112a, an intermediate portion 112b and a lower portion 112c. The upper portion 112a is formed as a tapered bore or a counter sinking hole which is inclined at a predetermined angle with respect to a center axis $CA_1$ so that the cross-sectional area thereof decreases toward the lower surface 104. The intermediate portion 112b is formed as a counter boring hole extending from the upper portion 112a at a right angle with respect to the upper surface 102 and the lower surface 104. The lower portion 112c is formed as a counter boring hole extending from the intermediate portion 112b at a right angle with respect to the upper surface 102 and the lower surface 104. The diameter $d_1$ of the intermediate portion 112b is larger than the diameter $d_2$ of the lower portion 112c. The lower portion 112c, namely the four-ridge internal thread 120, is connected to the intermediate portion 112b through a step 114 or a spot face in order to enlarge the diameter $d_2$ thereof. The start end portions 132 of the screw entry guide grooves 130 are connected to the step 114.

Figure 3B:
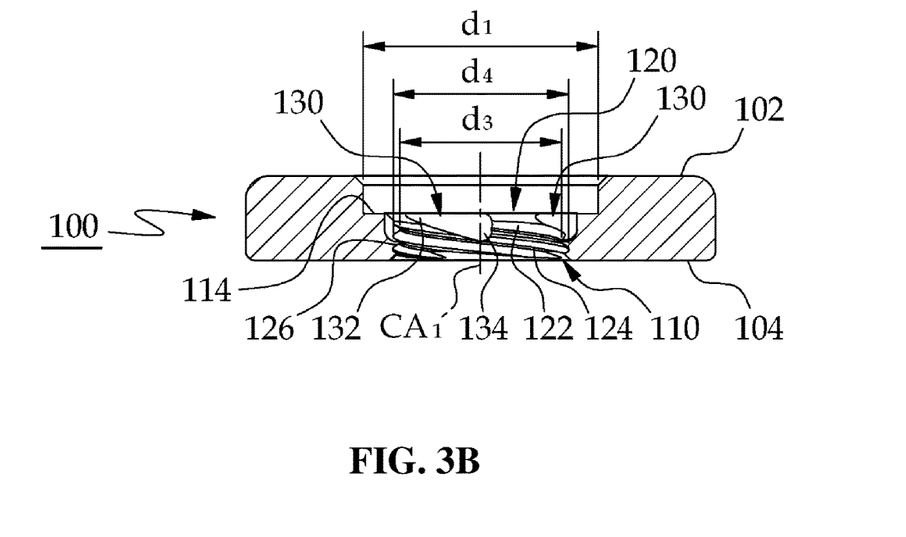

As illustrated in FIG. 3B, an internal thread is not formed in the upper portion 112a. The four-ridge internal thread 120 is formed in the lower portion 112c. The minor diameter $d_3$ of the four-ridge internal thread 120 is equal to the diameter $d_2$ of the lower portion 112c. The major diameter $D_4$ of the four-ridge internal thread 120 remains constant. In some embodiments, the intermediate portion 112b may be formed as a counter sinking hole.

Figure 4:
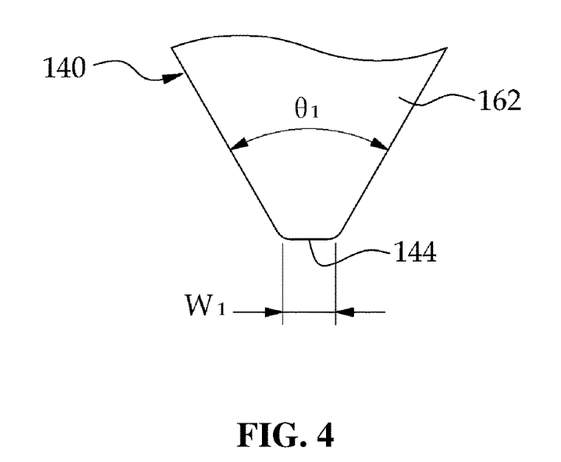
FIG. 4 is a view partially illustrating a nose portion of a cutting tool for forming the locking hole shown in FIG. 3.

In FIG. 4, there is illustrated a cutting tool used in forming the internal thread according to the present invention. Referring to FIG. 4, an internal thread forming cutting tool 140 includes a nose 142 for forming the four-ridge internal thread 120. A nose tip 144 has a predetermined width $W_1$. The angle of thread depends on the angle $\theta_1$ of the nose 142. If the width $W_1$ of the nose tip 144 is set small with respect to the same angle $\theta_1$ of the nose 142, an internal thread having a deep valley is formed. On the other hand, if the width $W_1$ of the nose tip 144 is large, an internal thread having a shallow valley is formed. In the present embodiment, the four-ridge internal thread 120 is formed by the internal thread forming cutting tool 140, the angle $\theta_1$ of the nose 142 of which is 60 degrees and the width $W_1$ of the nose tip 144 of which is about 0.16 mm.

Figure 5:
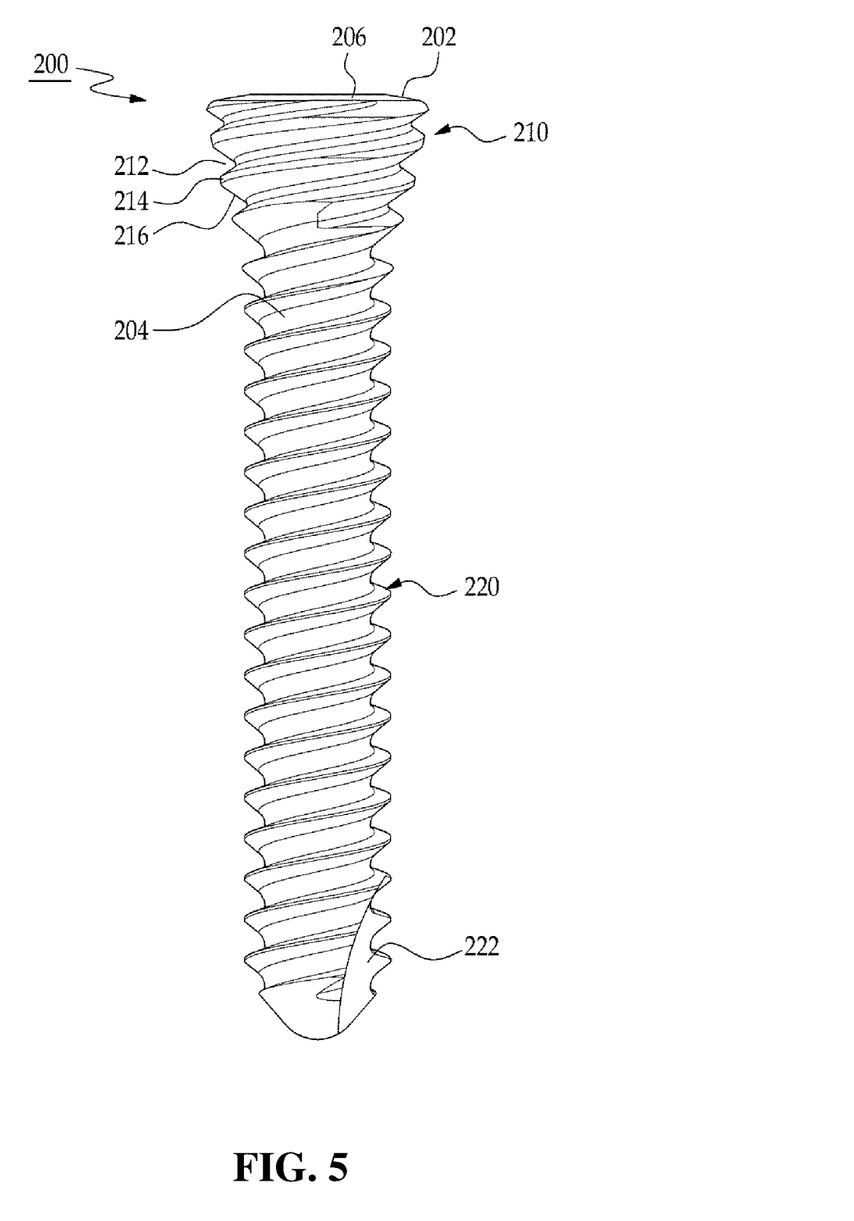
FIG. 5 is a front view illustrating a locking screw employed in the bone plate system according to the present invention.

Referring to FIGS. 1 and 5, the bone plate system according to the present invention includes a locking screw 200. The locking screw 200 includes a head 202 and a shank 204 extending from the head 202 in the axial direction. Similar to the bone plate 100, the locking screw 200 may be made of titanium. The head 202 is formed of a round head having a round upper surface 206. The height of the head 202 is about 1.2 mm or less.

A double-ridge external thread 210 is formed on the head 202 so that the double-ridge external thread 210 can be tightened to the four-ridge internal thread 120. The double-ridge external thread 210 includes a plurality of valleys 212, a plurality of ridges 214, and a plurality of flanks 216 which interconnects the valleys 212 and the ridges 214 adjoining each other. An external thread 220 is formed along an outer circumferential surface of the shank 204 so that the external thread 220 can be fastened to a bone. The double-ridge external thread 210 and the external thread 220 are formed so that they extend continuously. A flute 222 is formed in a distal end portion of the shank 204 so as to perform self-tapping or self-drilling.

Figure 6A:
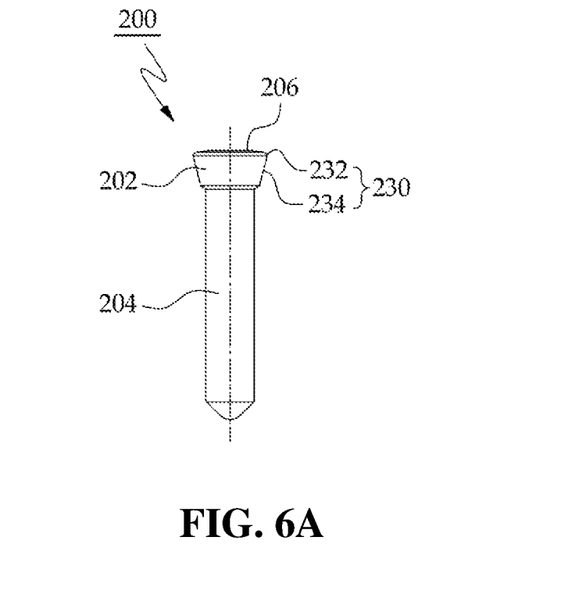
FIGS. 6A to 6E are views for explaining a process of forming the locking screw shown in FIG. 5.

The locking screw will be described in more detail with reference to FIGS. 6A to 6E. The locking screw 200 illustrated in FIG. 6A is in a state in which the double-ridge external thread 210 and the external thread 220 are not formed as yet. A thread formation portion 230 tapered at a predetermined angle with respect to a center axis $CA_2$ is formed on the outer circumferential surface of the head 202 of the locking screw 200. The thread formation portion 230 has an inverted con frustum shape which is tapered so that the diameter thereof decreases along the center axis $CA_2$. The thread formation portion 230 includes an upper thread formation portion 232 and a lower thread formation portion 234 extending from the upper thread formation portion 232 and tapered so that the diameter thereof decreases.

Figure 6B:
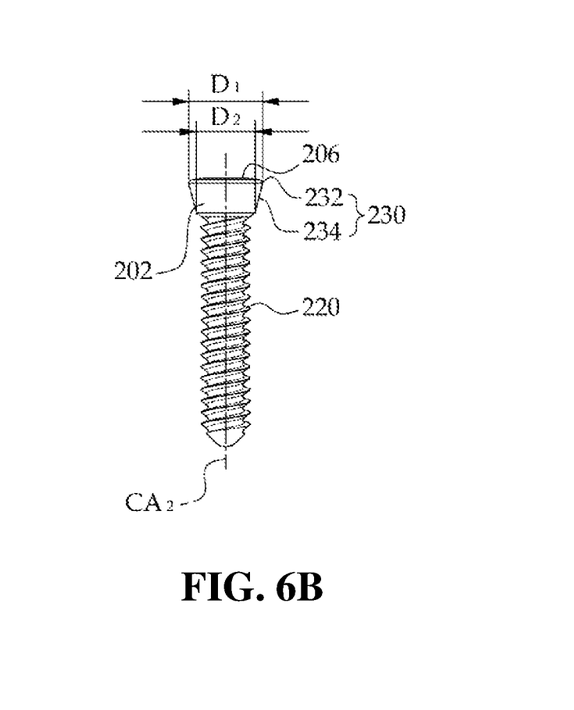
Figure 6C:
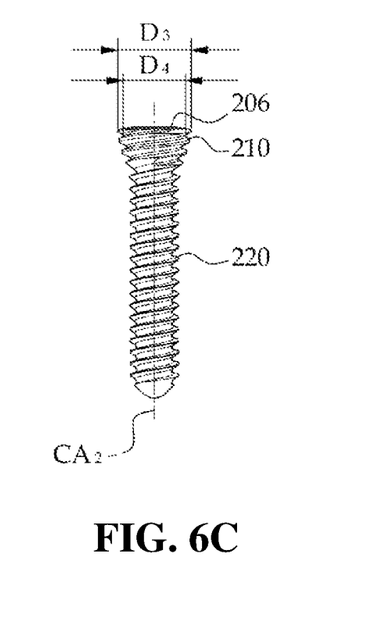

FIG. 6B illustrates a state in which the external thread 220 is formed on the shank 204 of the locking screw 200. The thread formation portion 230 has a maximum diameter $D_1$ and a minimum diameter $D_2$. FIG. 6C illustrates a state in which the double-ridge external thread 210 is formed on the thread formation portion 230. The maximum major diameter $D_3$ of the double-ridge external thread 210 is equal to the maximum diameter $D_1$ of the thread formation portion 230. The minimum major diameter $D_4$ of the double-ridge external thread 210 is equal to the minimum diameter $D_2$ of the thread formation portion 230.

Figure 6D:
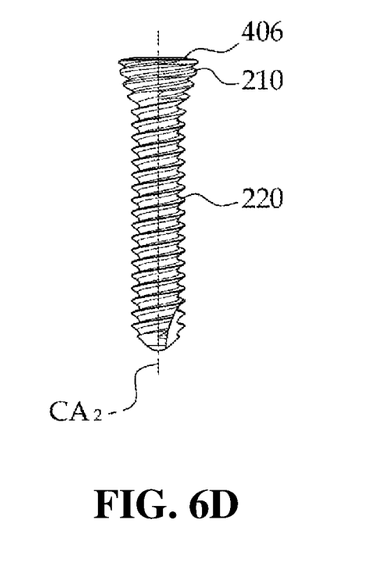
Figure 6E:
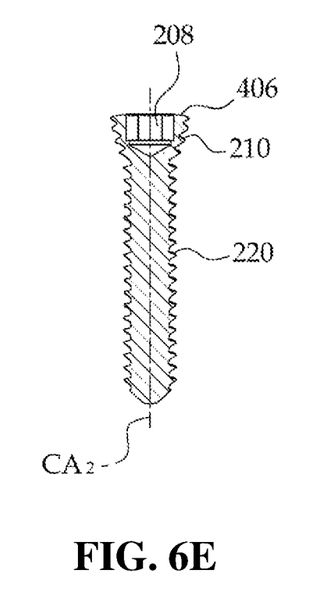

FIG. 6D illustrates a state in which the flute 222 is formed in the distal end portion of the shank 204. FIG. 6E illustrates a state in which a recess 208 for accommodating a tool for driving the locking screw 200 into a bone or tightening the locking screw 200 into the four-ridge internal thread 120, for example, a screw driver, is formed on an upper surface 206 of the head 202.

Figure 7:
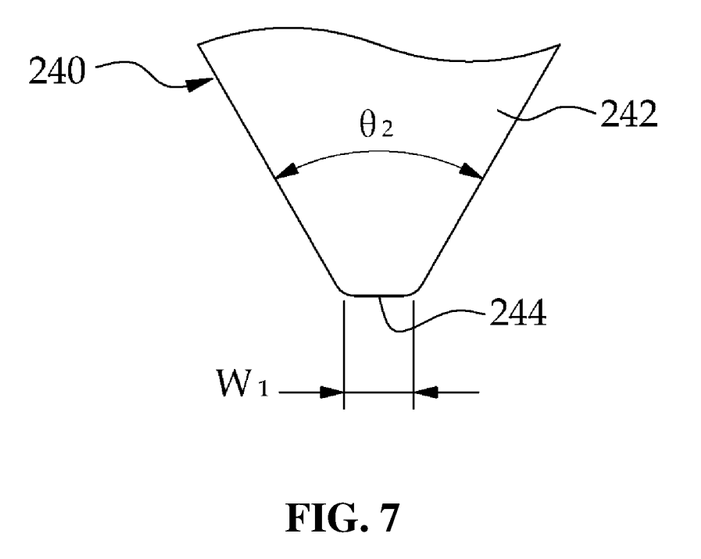
FIG. 7 is a view partially illustrating a nose portion of a cutting tool for forming the locking screw shown in FIG. 6.

In FIG. 7, there is illustrated a cutting tool used in forming the double-ridge external thread of the locking screw according to the present invention. Referring to FIG. 7, an external thread forming cutting tool 240 includes a nose 242 for forming the double-ridge external thread 210. A nose tip 244 has a predetermined width $W_2$. The angle of thread depends on the angle $\theta_2$ of the nose 242. If the width $W_2$ of the nose tip 244 is set small with respect to the same angle $\theta_2$ of the nose 242, an external thread having a deep valley is formed. On the other hand, if the width $W_2$ of the nose tip 244 is large, an external thread having a shallow valley is formed. The width $W_1$ of the nose tip 144 of the internal thread forming cutting tool 160 is larger than the width $W_2$ of the nose tip 244 of the external thread forming cutting tool 240. In the present embodiment, the double-ridge external thread 210 is formed by the external thread forming cutting tool 240, the angle $\theta_2$ of the nose 242 of which is 60 degrees and the width $W_2$ of the nose tip 244 of which is about 0.1 mm.

Figure 8:
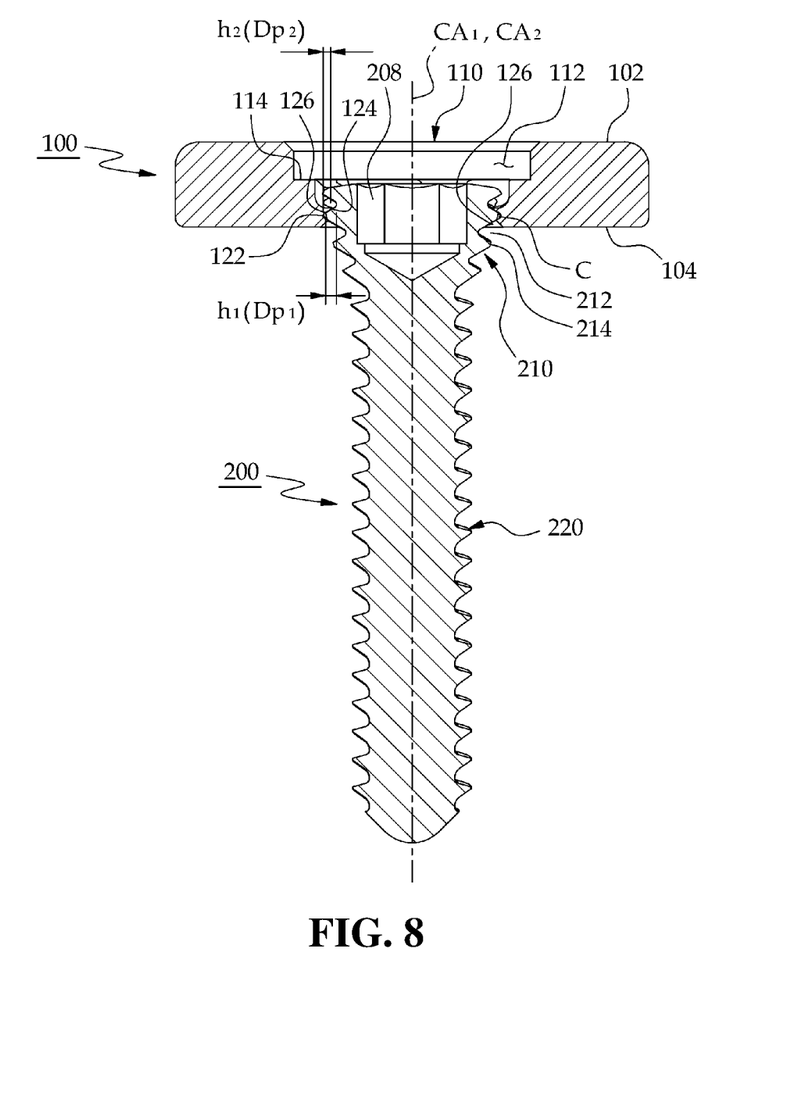
FIG. 8 is a sectional view illustrating a state in which the locking screw is concentrically tightened to the locking hole in the bone plate system according to the present invention.

FIG. 8 illustrates a state in which the locking screw is tightened to the internal thread of the bone plate in a right direction in the bone plate system according to the present invention. As described above, the width $W_1$ of the nose tip 144 of the internal thread forming cutting tool 160 is larger than the width $W_2$ of the nose tip 244 of the external thread forming cutting tool 240. Thus, the thread height $h_1$ of the double-ridge external thread 210 is larger than the thread height $h_2$ of the four-ridge internal thread 120. That is to say, the valley depth $DP_1$ of the valley having the maximum major diameter among the valleys 212 of the double-ridge external thread 210 is larger than the ridge height $h_2$ of the ridges 144 of the four-ridge internal thread 120 and is larger than the valley depth $DP_2$ of the valleys 142. The thread height $h_1$ of the double-ridge external thread 210 is substantially equal to the valley depth $DP_1$. The ridge height $h_2$ of the ridges 144 of the four-ridge internal thread 120 is substantially equal to the valley depth $DP_2$.

When tightening the double-ridge external thread 210, a gap exists between the double-ridge external thread 210 and the four-ridge internal thread 120. If the locking screw 200 is turned in a state in which the center axis $CA_1$ of each of the locking holes 110 and the center axis $CA_2$ of the locking screw 200 are coaxially disposed, the flanks 146 of the four-ridge internal thread 120 and the flanks 416 of the double-ridge external thread 210 make contact with each other. Gaps C are formed between the valleys 142 of the four-ridge internal thread 120 and the ridges 214 of the double-ridge external thread 210. Since the head 202 has an inverted cone frustum shape, the gap closer to the shank 204 has a larger size (volume).

In the meantime, in order to increase the fixing force provided by the coupling of the bone plate 100 and the locking screw 200, it is necessary to increase the length of the internal thread to which the locking screw is tightened. In order to increase the length of the internal thread, it is necessary to increase the thickness of the bone plate 100. In the bone plate system according to the present invention, the fixing force for fracture surgery can be kept large by the coupling of the four-ridge internal thread 120 and the double-ridge external thread 210. This makes it possible to reduce the thickness of the bone plate 100.

Figure 9:
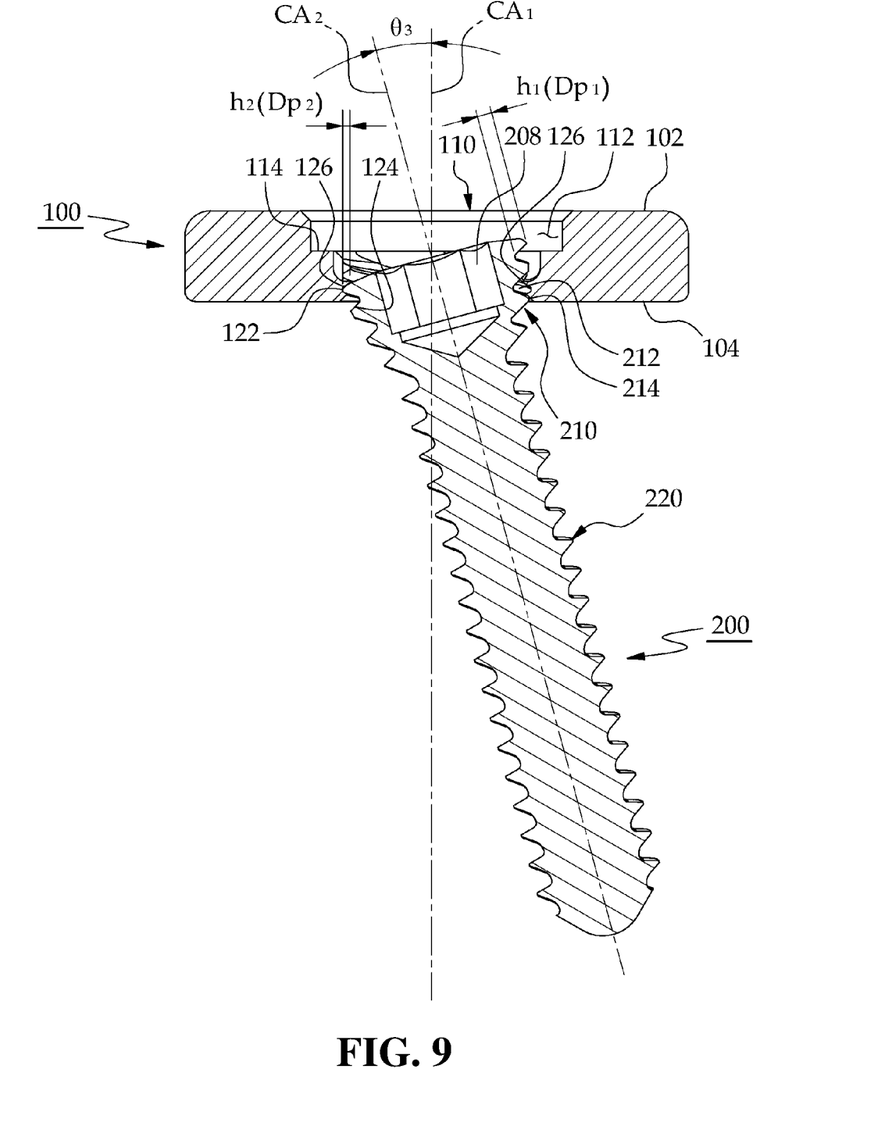
FIG. 9 is a sectional view illustrating a state in which the locking screw is obliquely tightened to the locking hole in the bone plate system according to the present invention.

FIG. 9 illustrates a state in which the locking screw is tightened to the internal thread of the bone plate in an oblique direction in the bone plate system according to the present invention. Referring to FIG. 9, the locking screw 200 may be tightened to the locking hole 110 with the center axis $CA_2$ thereof inclined with respect to the center axis $CA_1$ of the locking hole 110 at an arbitrary angle within a predetermined angular range $\theta_3$. In the present embodiment, the angular range $\theta_3$ is 60 degrees and the one side angular range is 30 degrees. The double-ridge external thread 210 is formed on the head 202 having an inverted cone frustum shape. The major diameter of the double-ridge external thread 210 decreases toward the shank 204. Thus, the gap between the double-ridge external thread 210 and the four-ridge internal thread 120 grows larger as the double-ridge external thread 210 comes closer to the shank 204. Accordingly, the double-ridge external thread 210 can be obliquely tightened to the four-ridge internal thread 120 formed in the lower portion 112c perpendicular to the upper surface 102 and the lower surface 104 of the bone plate 100.

The maximum value of the angular range $\theta_3$ over which the double-ridge external thread 210 can be obliquely tightened to the four-ridge internal thread 120 is limited by the size of the gaps C. The size of the gaps C is limited by the width $W_1$ of the internal thread forming cutting tool 160 and the width $W_2$ of the external thread forming cutting tool 240. Furthermore, the size of the gaps C is limited by the degree of taper of the thread formation portion 230. In some embodiments, the ratio of the width $W_1$ of the internal thread forming cutting tool 160 to the width $W_2$ of the external thread forming cutting tool 240 may be set to fall within a range of about 1.2 to 1.8.

In the case where the locking screw 200 is tightened in a state in which the locking screw 200 is inclined to one side with respect to the center axis $CA_1$ of the locking hole 110, the ridges 214 of the external thread 220 may interfere with the step 144 or the ridges 124 of the four-ridge internal thread 120 and may not be accurately moved into the valleys 122. When the locking screw 200 begins to be obliquely tightened, the screw entry guide grooves 130 formed in the portions where the tightening of the four-ridge internal thread 120 and the double-ridge external thread 210 begins can guide the ridges 214 of the double-ridge external thread 210 so as to smoothly move into the valleys 122 of the four-ridge internal thread 120. That is to say, the ridges 214 of the double-ridge external thread 210 are moved into the screw entry guide grooves 130 and are then guided toward the valleys 122 of the four-ridge internal thread 120. It is therefore possible to easily and accurately tighten the double-ridge external thread 210 to the four-ridge internal thread 120. Moreover, the angular range $\theta_3$ over which the double-ridge external thread 210 can be obliquely tightened to the four-ridge internal thread 120 is increased by the screw entry guide grooves 130.

In the case where the locking screw 200 is obliquely tightened, a portion of the double-ridge external thread 210 of the locking screw 200 is coupled to some of the valleys 122 of the four-ridge internal thread 120 and is accommodated in the intermediate portion 112b. By obliquely tightening the locking screw 200 in this way, it is possible to avoid interference between the locking screws 200 fastened to a bone during a surgical operation and to fix bone fragments in a direction effective for fracture surgery.

While preferred embodiments of the present invention have been described above, the present invention is not limited to the aforementioned embodiments. It goes without saying that a person skilled in the relevant art can make various changes and modifications without departing from the scope of the invention defined in the claims. Such changes and modifications shall be construed to fall within the scope of the present invention.

What is claimed is:

1. A bone plate system, comprising:
a bone plate including an upper surface, a lower surface configured to face a bone, and a locking hole in which an even-number-ridge internal thread is formed; and
a locking screw configured to be coupled to the locking hole, the locking screw including a head tapered so that a diameter thereof decreases along a center axis, a shank extending from the head, a double-ridge external thread formed on the head and configured to be tightened to the even-number-ridge internal thread, and an external thread formed on the shank and configured to be fastened to the bone,
wherein the even-number-ridge internal thread and the double-ridge external thread are equal in lead to each other,
a depth of a valley having a maximum major diameter among valleys of the double-ridge external thread is set larger than a height of each of ridges of the even-number-ridge internal thread so that when the double-ridge external thread is tightened to the even-number-ridge internal thread, the locking screw is obliquely tightened with respect to a center axis of the locking hole, and
a plurality of screw entry guide grooves is formed at ridge start points of the even-number-ridge internal thread so as to guide entry of the double-ridge external thread,
wherein the locking hole includes a bore extending through the upper surface and the lower surface, the bore including an upper portion tapered in a cone frustum shape and a lower portion not tapered, the even-number-ridge internal thread formed on an inner circumferential surface of the lower portion,
wherein the bore further includes a non-tapered intermediate portion disposed between the upper portion and the lower portion, the even-number-ridge internal thread connected to the intermediate portion via a step in order to enlarge a diameter, and
wherein each of the screw entry guide grooves includes a start end portion connected to the step.

2. The system of claim 1, wherein each of the screw entry guide grooves is formed to extend along a lead angle of the even-number-ridge internal thread, each of the screw entry guide grooves including a start end portion and a terminal end portion, the terminal end portion being larger in depth than the start end portion.

3. The system of claim 2, wherein each of the screw entry guide grooves has a width gradually increasing from the start end portion toward the terminal end portion.

4. The system of claim 1, wherein the head is tapered in an inverted cone frustum shape.

5. The system of claim 1, wherein a major diameter of the even-number-ridge internal thread is substantially equal to a maximum major diameter of the double-ridge external thread, and
a minor diameter of the even-number-ridge internal thread is larger than a minimum major diameter of the double-ridge external thread.

6. The system of claim 1, wherein the double-ridge external thread is formed by a nose tip of an external thread forming cutting tool, which is smaller in width than a nose tip of an internal thread forming cutting tool for forming the even-number-ridge internal thread.

* * * * *